United States Patent
Yanagida et al.

(10) Patent No.: US 12,029,530 B2
(45) Date of Patent: *Jul. 9, 2024

(54) INFORMATION PROCESSING METHOD, INFORMATION PROCESSING DEVICE, AND INFORMATION PROCESSING SYSTEM

(71) Applicant: Panasonic Intellectual Property Management Co., Ltd., Osaka (JP)

(72) Inventors: Masaaki Yanagida, Kyoto (JP); Masato Suzuki, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 15 days.

This patent is subject to a terminal disclaimer.

(21) Appl. No.: 17/884,267

(22) Filed: Aug. 9, 2022

(65) Prior Publication Data
US 2022/0378298 A1 Dec. 1, 2022

Related U.S. Application Data

(63) Continuation of application No. 16/704,135, filed on Dec. 5, 2019, now Pat. No. 11,445,920, which is a (Continued)

(30) Foreign Application Priority Data

Jun. 23, 2017 (JP) .................................. 2017-123223
Apr. 18, 2018 (JP) .................................. 2018-079949

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0022* (2013.01); *A61B 5/0261* (2013.01);
(Continued)

(58) Field of Classification Search
CPC ... A61B 5/0205; A61B 5/0022; A61B 5/0261; A61B 5/14546; A61B 5/14552;
(Continued)

(56) References Cited

U.S. PATENT DOCUMENTS 10,791,982 B2    10/2020  Littell
11,445,920 B2 *  9/2022   Yanagida ............... A61B 5/165
(Continued)

FOREIGN PATENT DOCUMENTS

JP    2002-143097    5/2002
JP    2003-337102    11/2003
(Continued)

OTHER PUBLICATIONS

International Search Report of PCT application No. PCT/JP2018/019002 dated Jun. 26, 2018.
(Continued)

*Primary Examiner* — Jonathan T Kuo
(74) *Attorney, Agent, or Firm* — Rimon P.C.

(57) ABSTRACT

An information processing method includes: obtaining first image data indicating an image of at least one portion of a face of a target person from a camera connected to or built into a first computer; obtaining cerebral blood flow information indicating a state of cerebral blood flow of the target person from a detector that is connected to or built into the first computer and that detects the cerebral blood flow information; and displaying, on a display connected to or built into a second computer connected to the first computer through a remote network, an output image including a first image based on the first image data and a second image
(Continued)

based on the cerebral blood flow information. The first image is a moving image including the at least one portion of the face, and the second image indicates changes over time in the cerebral blood flow information.

9 Claims, 12 Drawing Sheets

Related U.S. Application Data continuation of application No. PCT/JP2018/019002, filed on May 17, 2018.

(51) Int. Cl.
*A61B 5/026* (2006.01)
*A61B 5/103* (2006.01)
*A61B 5/145* (2006.01)
*A61B 5/1455* (2006.01)
*A61B 5/16* (2006.01)
*G06V 40/16* (2022.01)

(52) U.S. Cl.
CPC ........ *A61B 5/1032* (2013.01); *A61B 5/14546* (2013.01); *A61B 5/14552* (2013.01); *A61B 5/165* (2013.01); *A61B 5/6803* (2013.01); *A61B 5/7275* (2013.01); *A61B 5/743* (2013.01); *A61B 5/7475* (2013.01); *G06V 40/176* (2022.01); *A61B 5/0077* (2013.01)

(58) Field of Classification Search
CPC ... A61B 5/6803; A61B 5/7275; A61B 5/7475; A61B 5/0077; G16H 50/00–50/80; G06T 2207/30196–2207/30201
See application file for complete search history.

(56) References Cited

U.S. PATENT DOCUMENTS

| | | | |
|---|---|---|---|
| 2004/0152060 A1* | 8/2004 | Ando | G09B 7/00 434/362 |
| 2013/0251231 A1 | 9/2013 | Goto et al. | |
| 2014/0276014 A1* | 9/2014 | Khanicheh | A61B 5/0073 600/425 |
| 2015/0173618 A1 | 6/2015 | Kusukame | |
| 2016/0358332 A1 | 12/2016 | Watanabe | |
| 2017/0049377 A1* | 2/2017 | Littell | A61B 5/032 |
| 2017/0332965 A1 | 11/2017 | Hasegawa et al. | |

FOREIGN PATENT DOCUMENTS

| | | |
|---|---|---|
| JP | 2003-339648 A | 12/2003 |
| JP | 2004-255075 | 9/2004 |
| JP | 2009-268707 | 11/2009 |
| JP | 2014-023866 | 2/2014 |
| JP | 2015-116213 A | 6/2015 |
| JP | 2015-134157 | 7/2015 |
| JP | 2016-007300 | 1/2016 |
| JP | 2017-000743 | 1/2017 |
| JP | 2017-144225 | 8/2017 |
| WO | 2012/074039 A1 | 6/2012 |
| WO | 2016/084834 | 6/2016 |

OTHER PUBLICATIONS

English Translation of Chinese Search Report dated May 26, 2022 for the related Chinese Patent Application No. 201880027442.1.
Non-Final Office Action dated Feb. 2, 2022 issued in U.S. Appl. No. 16/704,135.
Notice of Allowance dated May 19, 2022 issued in U.S. Appl. No. 16/704,135.

* cited by examiner

INFORMATION PROCESSING METHOD, INFORMATION PROCESSING DEVICE, AND INFORMATION PROCESSING SYSTEM

CROSS-REFERENCE TO RELATED APPLICATIONS

This application is a continuation of U.S. patent application Ser. No. 16/704,135, filed on Dec. 5, 2019, which is a continuation of International Patent Application No. PCT/JP2018/019002, filed on May 17, 2018, which claims priority to Japanese Patent Application No. 2017-123223, filed on Jun. 23, 2017, and Japanese Patent Application No. 2018-079949, filed on Apr. 18, 2018, the entire disclosures each of which are hereby incorporated by reference.

BACKGROUND

1. Technical Field

The present disclosure relates to an information processing method, an information processing device, and an information processing system for performing diagnosis by utilizing biometric information of a target person.

2. Description of the Related Art

Recent years have seen shortages of hospitals and physicians mainly in regions other than urban areas. Remote diagnosis over a network is considered to be promising as measures against the shortages.

In diagnosis of mental disorders, physicians diagnose diseases based on facial expressions, the line-of-sights, and the facial colors of patients through medical interviews. Meanwhile, near-infrared spectroscopy (NIRS) devices, which are devices utilizing NIRS, are used as auxiliary tools for diagnosis. Each NIRS device illuminates a target portion of a target person with light, such as near-infrared light, and detects light that returns from the target portion, to thereby obtain information of blood flow of the target portion.

Use of the NIRS devices makes it possible to non-invasively detect changes in cerebral blood flow of target people. Diagnosis utilizing NIRS is performed, for example, in the following manner. First, a patient performs a task for diagnosis, while wearing an NIRS device. Prior to and subsequent to the task, the NIRS device is used to measure changes over time in light that has propagated in blood of the brain, an intensity distribution of the light, and so on. Based on these pieces of measured information, a physician diagnoses whether or not the target person has a mental disorder and the type of mental disorder.

Japanese Unexamined Patent Application Publication No. 2014-023866 discloses one example of a brain-activity-state analyzing method utilizing an NIRS device.

SUMMARY

In one general aspect, the techniques disclosed here feature an information processing method including: obtaining first image data indicating an image of at least one portion of a face of a target person from a first camera connected to or built into a first computer; obtaining cerebral blood flow information indicating a state of cerebral blood flow of the target person from a detector that is connected to or built into the first computer and that detects the cerebral blood flow information; and displaying, on a display connected to or built into a second computer connected to the first computer through a remote network, an output image including a first image based on the first image data and a second image based on the cerebral blood flow information. The first image is a moving image including the at least one portion of the face of the target person; and the second image indicates changes over time in the cerebral blood flow information.

It should be noted that general or specific embodiments may be implemented as a device, a system, a method, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
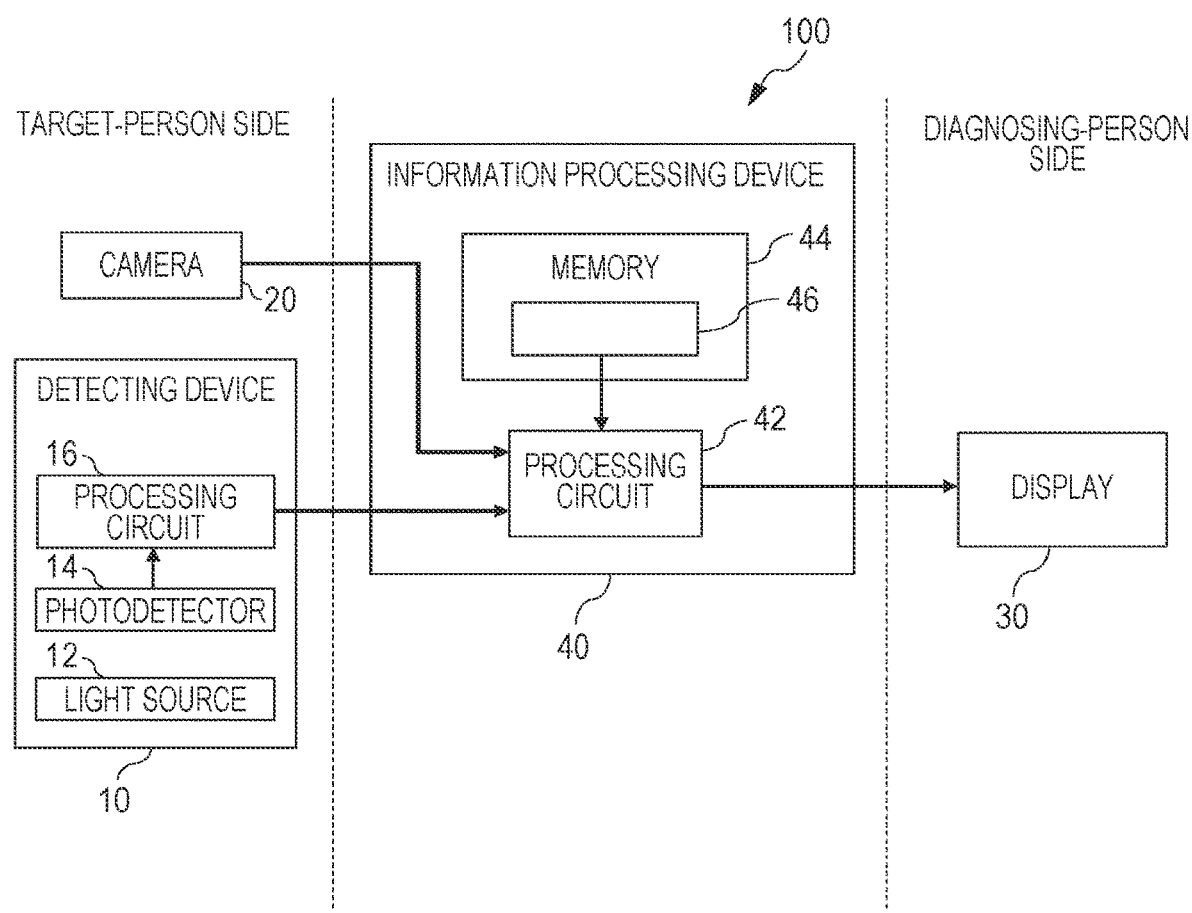
FIG. 1 is a block diagram schematically illustrating the configuration of an information processing system in an exemplary embodiment of the present disclosure.

Traditional medical interviews or diagnoses using NIRS devices need to be performed face-to-face between a diagnosing person (e.g., a physician) and a target person (e.g., a patient). However, owing to a shortage of hospitals or physicians in recent years, as described above, there are demands for remote medical diagnosis. An embodiment of the present disclosure provides an information processing method that is particularly effective for remote diagnosis. The technology disclosed herein can also be applied to cases in which a diagnosing person and a target person are near each other.

The embodiment of the present disclosure includes, for example, an information processing method, an information processing device, and an information processing system described below.

[First Item]

An information processing method according to a first item includes: obtaining first image data indicating an image of at least one portion of the face of a target person from a first camera connected to or built into a first computer; obtaining cerebral blood flow information indicating a state of cerebral blood flow of the target person from a detector that is connected to or built into the first computer and that detects the cerebral blood flow information; and displaying, on a display connected to or built into a second computer connected to the first computer through a remote network, an output image including a first image based on the first image data and a second image based on the cerebral blood flow information. The first image is a moving image including the at least one portion of the face of the target person; and the second image indicates changes over time in the cerebral blood flow information.

In this information processing method, an output image including a moving image of the face of a target person and changes over time in cerebral blood flow information of the target person is transmitted through a remote network and is displayed on the display of the second computer connected to the first computer. This allows a diagnosing person who operates the second computer to effectively perform remote diagnosis of the target person.

[Second Item]

In the information processing method according to the first item, the first image may indicate at least one selected from the group consisting of a change in a facial expression of the target person, a change in a line-of-sight of the target person, and a change in facial color of the target person.

This allows the diagnosing person to effectively perform remote diagnosis of the target person.

[Third Item]

In the information processing method according to the first or second item, the second image may include a graph indicating changes over time in numerically expressed cerebral blood flow information.

This allows the diagnosing person to effectively perform remote diagnosis of the target person.

[Fourth Item]

The information processing method according to the third item may further include causing an output device connected to or built into the first computer to output task information indicating a task to be performed by the target person. The second image may further include an image indicating a correspondence relationship between the changes over time in the cerebral blood flow information and a period in which the task information is output.

This clarifies the changes over time in the cerebral blood flow information of the target person during execution of the task.

[Fifth Item]

The information processing method according to the fourth item may further include detecting a change that exceeds a reference from at least one piece of data selected from the group consisting of second image data from the first camera, third image data from a second camera connected to or built into the first computer, and audio data from a microphone connected to or built into the first computer. The second image may further include an image indicating a correspondence relationship between the changes over time in the cerebral blood flow information and a period in which the change is detected from the at least one piece of data.

This clarifies influences that an event has on changes over time in the cerebral blood flow information of the target person.

[Sixth Item]

The information processing method according to the third item may further include: selecting part of the cerebral blood flow information indicating cerebral blood flow information related to at least one specific region in a brain of the target person; and expressing the part as a graph.

Expressing the part of the cerebral blood flow information as a graph eliminates the need for extensively checking the cerebral blood flow information of the target person. As a result, the diagnosing person can effectively perform remote diagnosis of the target person.

[Seventh Item]

The information processing method according to the sixth item may further include: causing the display to display an item for determining the at least one specific region; and obtaining input information regarding the item from an input device connected to or built into the second computer. The at least one specific region may be determined according to the input information.

In this information processing method, when a cerebral region that becomes active greatly according to a disease or a symptom is known from statistical data, setting the cerebral region by using the input device makes it possible to easily determine the specific region.

[Eighth Item]

The information processing method according to the sixth item may further include causing an output device connected to or built into to the first computer to output preliminary task information indicating a preliminary task to be performed by the target person. The at least one specific region may be determined according to a change in the cerebral blood flow information with respect to the preliminary task information.

This determination method is effective when the cerebral region that becomes active according to a disease or a symptom is not known.

[Ninth Item]

The information processing method according to the first item may further include: selecting part of the cerebral blood flow information indicating cerebral blood flow information related to at least one specific region in a brain of the target person; and transmitting the part from the first computer to the second computer through the remote network.

This makes it possible to reduce the amount of communication from the first computer to the second computer. As a result, delay in the communication can be suppressed or reduced.

[Tenth Item]

The information processing method according to the ninth item may further include: causing the display to display an item for determining the at least one specific region; and obtaining input information regarding the item from an input device connected to or built into the second computer. The at least one specific region may be determined according to the input information.

In this information processing method, when a cerebral region that becomes active greatly according to a disease or a symptom is known from statistical data, setting the cerebral region by using the input device makes it possible to easily determine the specific region.

[11th Item]

The information processing method according to the ninth item may further include causing an output device connected to or built into to the first computer to output preliminary task information indicating a preliminary task to be performed by the target person. The at least one specific region may be determined according to a change in the cerebral blood flow information with respect to the preliminary task information.

This determination method is effective when the cerebral region that becomes active according to a disease or a symptom is not known.

[12th Item]

In the information processing method according to one of the first to third items, the output image may be obtained by combining the first image and the second image.

This allows the diagnosing person to effectively perform remote diagnosis while viewing both the face of the target person and the cerebral blood flow information thereof.

[13th Item]

In the information processing method according to the 12th item, the detector comprises: at least one light source that illuminates a target portion of a head portion of the target person with emission light; an image sensor that detects reflection light that returns from the target portion; and a processing circuit that generates the cerebral blood flow information for the target portion, based on information of the reflection light detected by the image sensor, and that outputs the cerebral blood flow information. The at least one light source may illuminate a plurality of regions in the target portion with the emission light. The image sensor may output a signal indicating an intensity distribution of the reflection light from the plurality of regions. The processing circuit may generate the cerebral blood flow information, based on the signal, and may output the cerebral blood flow information. The second image may indicate the changes over time in the cerebral blood flow information for the plurality of regions.

In this information processing method, a two-dimensional distribution of the target person's cerebral blood flow detected by the image sensor is combined with the moving image of the face of the target person and is displayed. This allows the diagnosing person to effectively perform remote diagnosis of the target person.

[14th Item]

In the information processing method according to the 13th item, the at least one light source may include: a first light source that illuminates the target portion with first emission light having a wavelength that is 650 nm or more and less than 805 nm; and a second light source that illuminates the target portion with second emission light having a wavelength that is larger than 805 nm and is 950 nm or less. The image sensor may output a first electrical signal corresponding to an amount of first reflection light that returns from the target portion as a result of the illumination of the first emission light and a second electrical signal corresponding to an amount of second reflection light that returns from the target portion as a result of the illumination of the second emission light. The processing circuit may generate, as the cerebral blood flow information, information indicating a concentration of oxygenated hemoglobin and a concentration of deoxygenated hemoglobin in cerebral blood in the target portion, based on the first electrical signal and the second electrical signal. The second image may include information indicating changes over time in at least one selected from a group consisting of the concentration of oxygenated hemoglobin in the target portion and the concentration of deoxygenated hemoglobin in the target portion.

In this information processing method, oxygenated hemoglobin and deoxygenated hemoglobin in cerebral blood of the target person can be obtained with the two light sources. This allows the diagnosing person to diagnose the state of the brain activity of the target person in detail.

[15th Item]

In the information processing method according to one of the first to 14th items, the second computer may switch an image displayed on the display in response to an operation on the second computer. The information processing method may further include: causing the first image to be displayed on the display; and causing the second image to be displayed on the display in addition to the first image or instead of the first image, in response to the operation.

In this information processing method, for example, when the diagnosing person performs an operation on the second computer, the second image can be displayed on the display in addition to or instead of the face image of the target person. This allows the diagnosing person to effectively perform remote diagnosis of the target person.

[16th Item]

In the information processing method according to the first to 15th item, the detector may be built into a head-mounted device connected to the first computer and worn on a head portion of the target person.

This makes it possible to reduce influences of ambient light, even for outdoor use.

[17th Item]

The information processing method according to one of the first to 16th items may further include: assessing at least one selected from a group consisting of a psychological state of the target person and a probability of the target person having a disease, based on the cerebral blood flow information; and displaying a result of the assessment on the display.

This allows the diagnosing person to effectively perform remote diagnosis of the target person.

[18th Item]

An information processing device according to an 18th item is an information processing device connected to a first computer and a second computer through a network and includes a processing circuit and a memory in which a computer program is stored. The computer program causes the processing circuit to execute: obtaining first image data indicating an image of at least one portion of the face of a target person from a camera connected to or built into the first computer; obtaining cerebral blood flow information indicating a state of cerebral blood flow of the target person from a detector that is connected to or built into the first computer and that detects the cerebral blood flow information; and displaying, on a display connected to or built into the second computer connected to the first computer through a remote network, an output image including a first image based on the first image data and a second image based on the cerebral blood flow information. The first image is a moving image including the at least one portion of the face of the target person; and the second image indicates changes over time in the cerebral blood flow information.

This allows a diagnosing person who operates the second computer to effectively perform remote diagnosis of the target person.

[19th Item]

An information processing system according to a 19th item includes the information processing device according to the 18th item and the display.

In this information processing system, by using the information processing device according to the 18th item and the display, the diagnosing person can effectively perform remote diagnosis of the target person.

[20th Item]

The information processing system according to the 19th item may further include the detector and the camera.

In this information processing system, by using the information processing device according to the 19th item, the output device, and the camera, the diagnosing person can effectively perform remote diagnosis of the target person.

In the present disclosure, all or a part of any of circuits, units, devices, parts, or portions or any of functional blocks in the block diagrams may be implemented as one or more of electronic circuits including, but not limited to, a semiconductor device, a semiconductor integrated circuit (IC), or a large-scale integration (LSI). The LSI or IC can be integrated into one chip or also can be a combination of a plurality of chips. For example, functional blocks other than a memory may be integrated into one chip. Although the name used here is LSI or IC, it may also be called system LSI, very large scale integration (VLSI), or ultra large scale integration (ULSI) depending on the degree of integration. A field programmable gate array (FPGA) that can be programmed after manufacturing an LSI or a reconfigurable logic device that allows reconfiguration of the connection or setup of circuit cells inside the LSI can also be used for the same purpose.

In addition, the functions or operations of all or a part of the circuits, units, devices, parts, or portions can be implemented by executing software. In such a case, the software is recorded on one or more non-transitory recording media, such as a ROM, an optical disk, or a hard disk drive, and when the software is executed by a processor, the software causes the processor together with peripheral devices to execute the functions specified in the software. A system or a device may include such one or more non-transitory recording media on which the software is recorded and a processor together with necessary hardware devices, such as an interface.

An embodiment of the present disclosure will be described below in detail. However, an overly detailed description may be omitted herein. For example, a detailed description of already well-known things and a redundant description of substantially the same configuration may be omitted herein. This is to avoid the following description becoming overly redundant and to facilitate understanding of those skilled in the art. The accompanying drawings and the following description are provided so as to allow those skilled in the art to fully understand the present disclosure and are not intended to limit the subject matters recited in the claims. In the following description, the same or similar constituent elements are denoted by the same reference numerals.

Embodiment

The present embodiment relates to an information processing method, an information processing device, and an information processing system for a diagnosing person (e.g., a physician) to remotely diagnose, for example, a psychological state of a target person (e.g., a patient). In the present embodiment, the diagnosing person and the target person are assumed to be at two locations (e.g., a hospital and the home of the target person) that are distant from each other. The two locations are connected to each other through a remote network.

The "remote network" means an information network that connects two distant sites. The remote network is, for example, the Internet or a wide area network (WAN), such as a dedicated line, and does not include a network constituted by only a local area network (LAN). The remote network may be implemented by a virtual private network (VPN).

The "psychological state" as used herein refers to a mood (e.g., comfort or discomfort), an emotion (e.g., relief, worry, sadness, or anger), a health condition (e.g., liveliness or fatigue), a thermal sensation (e.g., hot, cold, or muggy), a medical condition (e.g., mania, depression, or schizophrenia), or an index (e.g., the degree of proficiency, the degree of learning, or the degree of concentration) indicating the degree of a brain activity that derives therefrom. The psychological state can be assessed based on changes in a cerebral blood flow rate or changes in a component (e.g., hemoglobin) in blood. For example, when the activity of nerve cells changes in response to a change in the psychological state of a human, the cerebral blood flow rate or a component in blood changes. Accordingly, when a detecting device, such as an NIRS device, is used to measure biometric information, such as changes in a cerebral blood flow rate or changes in a component in blood, the psychological state of the target person can be assessed.

[Configuration]

FIG. 1 is a block diagram schematically illustrating the configuration of an information processing system 100 in the present embodiment. The information processing system 100 includes a detecting device 10, a camera 20, a display 30, and an information processing device 40. The detecting device 10 and the camera 20 are placed at a target-person side. The display 30 is placed at a diagnosing-person side. The information processing device 40 is connected to the detecting device 10, the camera 20, and the display 30 through a remote network. The information processing device 40 may be, for example, a server computer on the Internet. The technology disclosed herein can also be applied to cases in which the information processing device 40 is connected to the detecting device 10, the camera 20, or the display 30 through, for example, a network constituted by a LAN or a mere cable, rather than a remote network.

The detecting device 10 is, for example, an NIRS device and detects cerebral blood flow information of a target person 1. The detecting device 10 includes at least one light source 12, a photodetector 14, and a processing circuit 16. The camera 20 photographs the target person 1 to output image data. The image data indicates at least one of, for example, a facial expression, the line-of-sight, and facial color of the target person 1. The information processing device 40 generates information for diagnosing the psychological state of the target person 1, based on the cerebral blood flow information detected by the detecting device 10, and transmits the generated information to the display 30.

The information processing device 40 includes a processing circuit 42 and a memory 44. The memory 44 stores a computer program 46 therein. The computer program 46 causes the processing circuit 42 to execute processes (1) to (4) below:

(1) obtaining first image data indicating an image including at least one portion of the face of the target person 1 from the camera 20;
(2) obtaining cerebral blood flow information of the target person 1 from the detecting device 10;
(3) generating second image data including information for diagnosing the psychological state of the target person 1, based on the obtained cerebral blood flow information; and
(4) causing at least one image based on the first and second image data to be displayed on the display 30.

Processes (1) and (2) described above may be interchanged in order or may be performed at the same time.

In process (4) described above, the image that is displayed on the display 30 may be a combination of a first image based on the first image data, the first image being a face image of the target person, and a second image based on the second image data, the second image being an image indicating changes over time in the cerebral blood flow information. These two images may be displayed at the same time or may be displayed at different timings. Alternatively, one output image obtained by combining the two images together may be displayed. Each image that is displayed is not limited to a still image and may be a moving image. When the image that is displayed is a moving image, the first image may indicate at least one selected from a group consisting of, for example, a change in the facial expression, a change in the line-of-sight, and a change in the facial color of the target person 1. When the image that is displayed is a moving image, the second image may be an image indicating changes over time in numerically expressed cerebral blood flow information.

When a moving image is displayed, the information processing device 40 repeatedly executes processes (1) to (4) described above, for example, at regular time intervals. The regular time intervals depend on the frame rate of the moving image. For example, when a moving image having a frame rate of 30 frames per second (fps) is displayed, the information processing device 40 repeatedly executes processes (1) to (4) at intervals of $\frac{1}{30}$ second. When the intervals are sufficiently short, real-time remote diagnosis using a moving image is possible. The repetition intervals depend on throughput of each device and the bandwidth of a network. For example, the intervals may be set to 1 second or less or may be set to $\frac{1}{30}$ second or less. The intervals, however, are not limited to the aforementioned range. A camera image that is a moving image based on the first image data and a cerebral blood flow image that is a moving image based on the second image data may be displayed with different frame rates. For example, the camera image may be displayed with a frame rate of 30 fps or more, and the cerebral blood flow image may be displayed with a frame rate of several frames per second or more. Since the cerebral blood flow changes relatively slowly, there is practically no problem with the frame rate of the cerebral blood flow image even when it is lower than the frame rate of the camera image.

The processing circuit 42 in the information processing device 40 may be, for example, a processor, such as a central processing unit (CPU) or a graphics processing unit (GPU). A combination of a processor and a computer program realizes an information processing method in the present embodiment. The processing circuit 42 and the memory 44 may be realized by one integrated circuit. The processing circuit 42 may be realized by, for example, a digital signal processor (DSP) or a programmable logic device (PLD), such as a field programmable gate array (FPGA).

Figure 2:
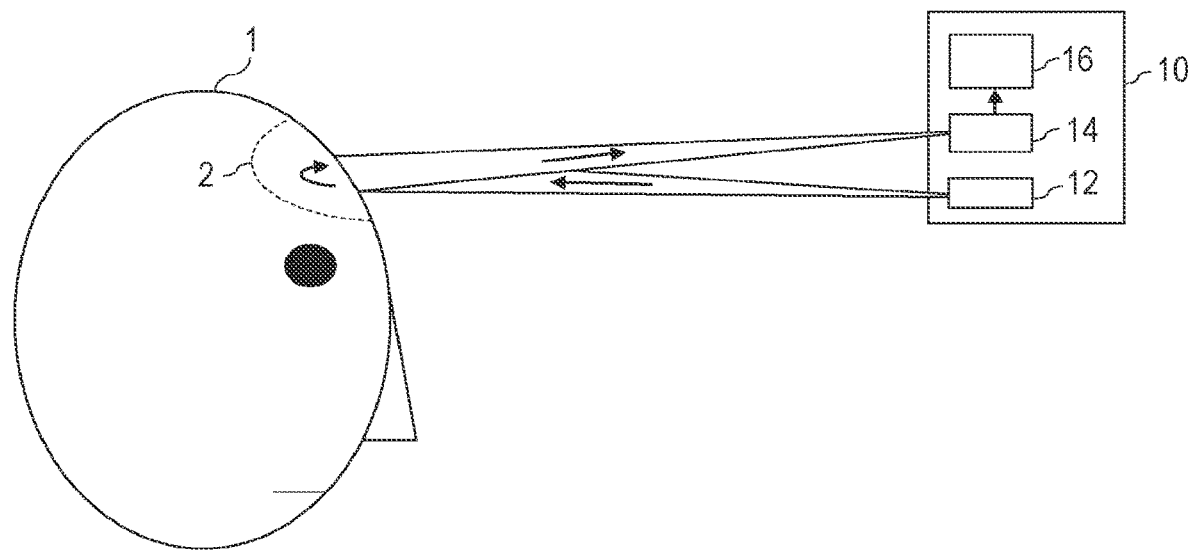
FIG. 2 is a diagram schematically illustrating a state in which a detecting device is used to detect cerebral blood flow information of a target portion of a target person.

FIG. 2 is a diagram schematically illustrating a state in which the detecting device 10 is used to detect the cerebral blood flow information of a target portion 2 of the target person 1. In the example illustrated in FIG. 2, the target portion 2 is the forehead portion of the target person 1. Although not illustrated in FIGS. 1 and 2, the detecting device 10 further includes a control circuit that synchronously controls the operation of a light source 12 and the operation of the photodetector 14. The number of light sources 12 differs depending on the application. For example, in an application in which the number of pulses at the target portion 2 is measured and an application in which changes over time in the concentration of oxygenated hemoglobin in cerebral blood are detected, a light source 12 having a single wavelength can be used. Meanwhile, in an application in which information on both the concentration of oxygenated hemoglobin and the concentration of deoxygenated hemoglobin in cerebral blood is obtained, two light sources that emit respective two types of light having different wavelengths may be used, as described below.

As illustrated in FIG. 2, the light source 12 emits light that illuminates the target portion 2 of a head portion of the target person 1. Part of light that is incident on the target portion 2 is scattered by tissue in the brain of the target person 1 and exits from the target portion 2. The light includes information indicating the state of blood in the brain. Upon receiving the light that has arrived from the target portion 2, the photodetector 14 outputs electrical signals corresponding to the amount of the received light. Based on the output electrical signals, the processing circuit 16 generates cerebral blood flow information of the target portion 2 and outputs the cerebral blood flow information.

The "cerebral blood flow information" as used herein refers to arbitrary information indicating the state of blood in the brain. The cerebral blood flow information may be, for example, raw data output from the photodetector 14 or data generated by processing raw data. The raw data output from the photodetector 14 means data indicating the amount of reflection light from at least one region of a target portion. When the photodetector 14 transmits the raw data to the information processing device 40, the processing circuit 16 transfers the raw data to the information processing device 40 without performing any particular processing on the raw data. The processing circuit 16 may generate, as the cerebral blood flow information, information indicating the concentration of at least one of oxygenated hemoglobin and deoxygenated hemoglobin in cerebral blood in the target portion 2. The processing circuit 16 may generate information about the number of pulses as the cerebral blood flow information. The processing circuit 42 in the information processing device 40, instead of the processing circuit 16, may perform processing for generating the cerebral blood flow information.

The photodetector 14 has at least one light-receiving element having sensitivity to light emitted from the light source 12. Typically, the photodetector 14 is an image sensor in which a plurality of light-receiving elements is arranged two-dimensionally. The individual light-receiving elements in the image sensor output electrical signals corresponding to the amounts of received light through photoelectric conversion. The collection of the electrical signals provides image signals.

The light source 12 emits, for example, light having a wavelength of 650 nm or more and 950 nm or less. This wavelength range is included in the wavelength range of red to near-infrared light. This wavelength range is called the biological window and is known to have a low in-vivo absorption rate. Although the light source 12 in the present embodiment is described as emitting light in the above-described wavelength range, it may use light in another wavelength range. Terms for "light" are also used herein not only for visible light but also for infrared light.

In a visible light region that is smaller than a wavelength of 650 nm, the rate of absorption by oxygenated hemoglobin ($HbO_2$) and the rate of absorption by deoxygenated hemoglobin (Hb) in blood are high, and in a wavelength range that is larger than 950 nm, the rate of absorption by water is high. On the other hand, in a wavelength range of 650 nm or more and 950 nm or less, the rates of absorption by oxygenated hemoglobin, deoxygenated hemoglobin, and water are relatively low, and the rates of scattering by oxygenated hemoglobin, deoxygenated hemoglobin, and water are relatively high. For a wavelength of 805 nm, the rate of absorption by oxygenated hemoglobin and the rate of absorption by deoxygenated hemoglobin become equal to each other.

Accordingly, when information on both the oxygenated hemoglobin and the deoxygenated hemoglobin is to be obtained, the light source 12 may be implemented by a first light source that emits light having a first wavelength that is 650 nm or more and is less than 805 nm and a second light source that emits light having a second wavelength that is larger than 805 nm and is 950 nm or less. For example, the first wavelength may be 750 nm, and the second wavelength may be 850 nm.

When light having two wavelengths is used as described above, the photodetector 14 is configured so as to individually detect the light having the wavelengths. For example, the photodetector 14 may include at least one photodiode and a plurality of charge accumulators. In this case, the light source 12 emits the light having two wavelengths at different timings, and in synchronization with the timing at which the light having the two wavelengths returns, signal charges resulting from the light are accumulated in two charge accumulators. This makes it possible to individually detect the light having the two wavelengths. In this case, the photodetector 14 outputs a first electrical signal corresponding to the amount of light having a first wavelength which arrives from the target portion 2 and a second electrical signal corresponding to the amount of light having a second wavelength which arrives from the target portion 2. By performing predetermined arithmetic operations based on the first and second electrical signals, the processing circuit 16 can determine the concentration of oxygenated hemoglobin and the concentration of deoxygenated hemoglobin in the target portion 2. In one example, the processing circuit 16 generates information of the concentrations as the cerebral blood flow information.

The processing circuit 42 in the information processing device 40 obtains the cerebral blood flow information from the processing circuit 16 and generates second image data including information for diagnosing the psychological state of the target person 1. The second image data may include, for example, information indicating changes over time in at least one of the concentration of oxygenated hemoglobin and the concentration of deoxygenated hemoglobin in the target portion 2. Such information is displayed on the display 30 to thereby allow the diagnosing person to diagnose the state of the brain activity of the target person in detail.

The detecting device 10 and the camera 20 may be connected to or built into a first computer operated by the target person 1. The display 30 may be connected to or built into a second computer operated by the diagnosing person. The first and second computers may be, for example, personal computers (PCs), tablet computers, or information equipment, such as smartphones. The first computer at the target-person side and the second computer at the diagnosing-person side may both have communication functions to connect to each other through a remote network. In such a configuration, the information processing device 40 may be a third computer connected to the first and second computers through a remote network. Alternatively, the second computer at the diagnosing-person side may function as the information processing device 40.

Figure 3:
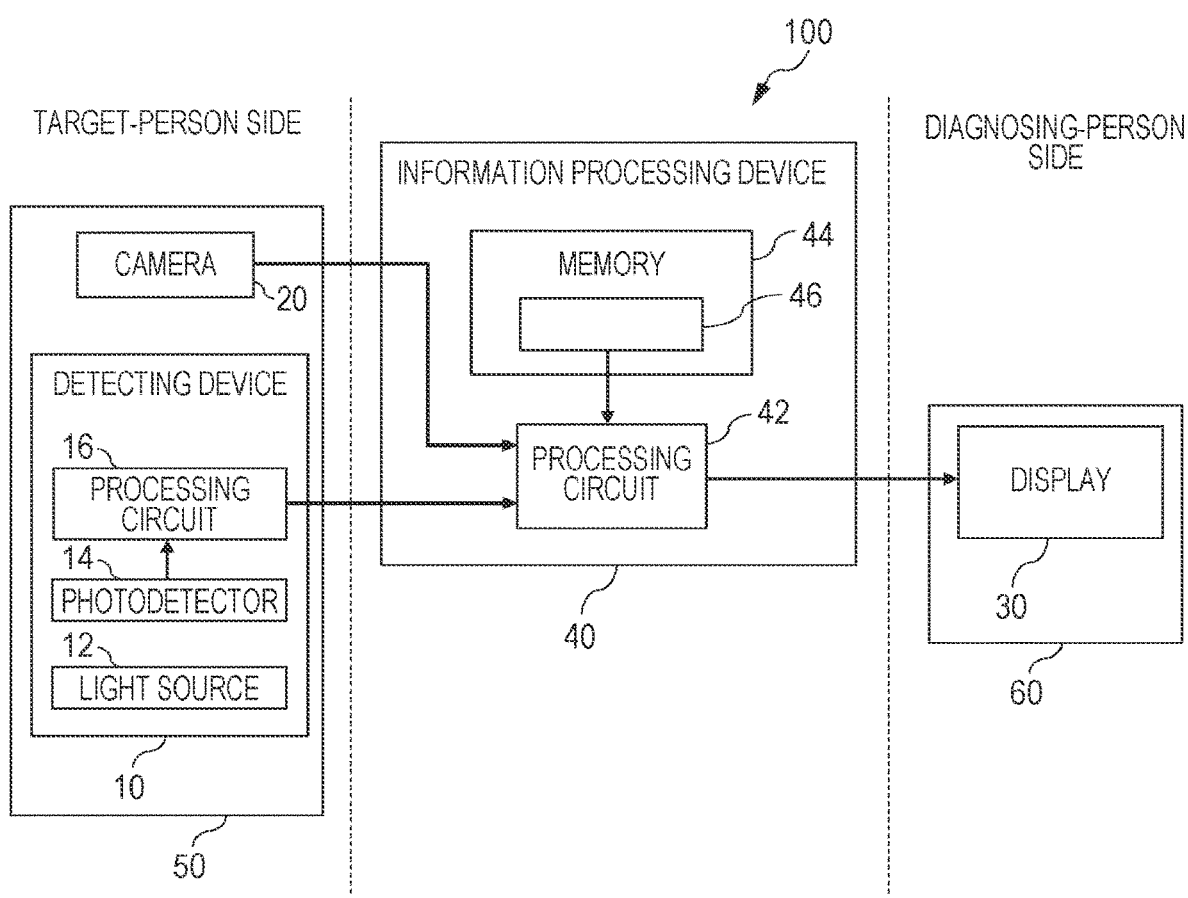
FIG. 3 is a block diagram illustrating an example of a configuration in which the detecting device is built into a target-person's computer, and a display is built into a diagnosing-person's computer.

FIG. 3 is a block diagram illustrating an example of a configuration in which the detecting device 10 is built into a target-person's computer 50, which is the first computer operated by the target person, and the display 30 is built into a diagnosing-person's computer 60, which is the second computer operated by the diagnosing person. In the example illustrated in FIG. 3, the camera 20 is also built into the target-person's computer 50. According to such a configuration, the target-person's computer 50 and the diagnosing-person's computer 60 are connected to the information processing device 40 via respective communication functions. Application software for implementing remote diagnosis is installed on the target-person's computer 50 and the diagnosing-person's computer 60. When the remote diagnosis is performed, the target person and the diagnosing person start up predetermined applications in the target-person's computer 50 and the diagnosing-person's computer 60, respectively, to perform video calling. In a configuration in which the target-person's computer 50 and the diagnosing-person's computer 60 are not provided, like that in FIG. 1, each of the camera 20, the detecting device 10, and the display 30 has a communication function to communicate with the information processing device 40.

A variety of variations are possible to the configuration of the target-person's computer 50, the detecting device 10, and the camera 20. Some examples of the variations will be described below.

Figure 4:
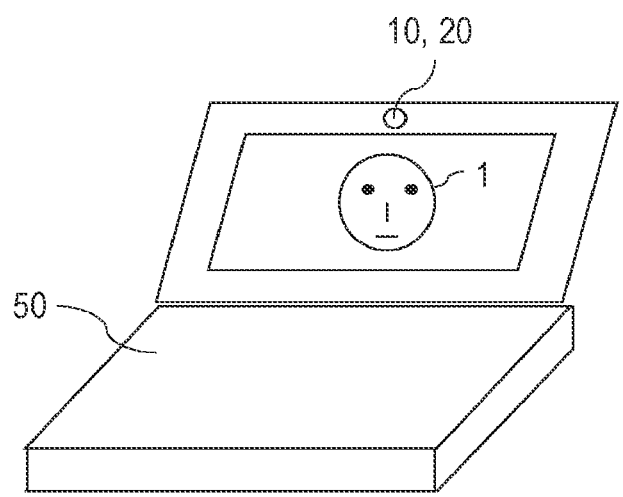
FIG. 4 is a view schematically illustrating one example of the configuration of the target-person's computer, the detecting device, and a camera.

FIG. 4 is a view schematically illustrating one example of the configuration of the target-person's computer 50, the detecting device 10, and the camera 20. In the example illustrated in FIG. 4, the target-person's computer 50 has the detecting device 10 and the camera 20 that are built therein. A face image of the target person 1 captured by the camera 20 is displayed on a display of the target-person's computer 50. This face image is the same as an image displayed on the display 30 of the diagnosing-person's computer 60. This allows the target person 1 to check his or her face image displayed on the display 30 of the diagnosing-person's computer 60. In a period in which the target person 1 and the diagnosing person are performing video calling, the face image of the target person 1 which is displayed on the target-person's computer 50 may be switched to a face image of the diagnosing person. The face image of the diagnosing person is an image captured by, for example, a camera (not illustrated) provided in the diagnosing-person's computer 60. In the example illustrated in FIG. 4, the detecting device 10 and the camera 20 are built into and integrated into the target-person's computer 50. Thus, the target-person's computer 50 is compact and is easy to carry. The target person can operate the detecting device 10, the camera 20, and the target-person's computer 50 by using a user interface, such as a keyboard or a mouse. Although a notebook PC is illustrated as one example of the target-person's computer 50 in the example illustrated in FIG. 4, the target-person's computer 50 may be a desktop PC. A tablet computer or a smartphone may be used instead of the PC.

Figure 5:
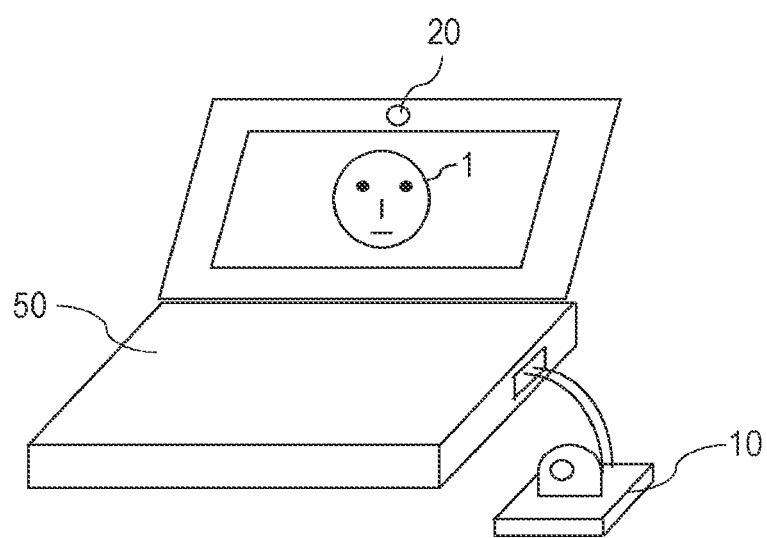
FIG. 5 is a view schematically illustrating another example of the configuration of the target-person's computer, the detecting device, and the camera.

FIG. 5 is a view schematically illustrating another example of the configuration of the target-person's computer 50, the detecting device 10, and the camera 20. In the example illustrated in FIG. 5, the detecting device 10 is an external device that is used through connection to the target-person's computer 50 into which the camera 20 is built. The connection between the detecting device 10 and the target-person's computer 50 is realized by, for example, a cable that complies with a known standard, such as a Universal Serial Bus (USB) standard. Since the detecting device 10 is external equipment, the connection can be realized by merely adding execution software to the target-person's computer 50, which is already available. Also, there is an advantage in that only the detecting device 10 can be carried.

Figure 6:
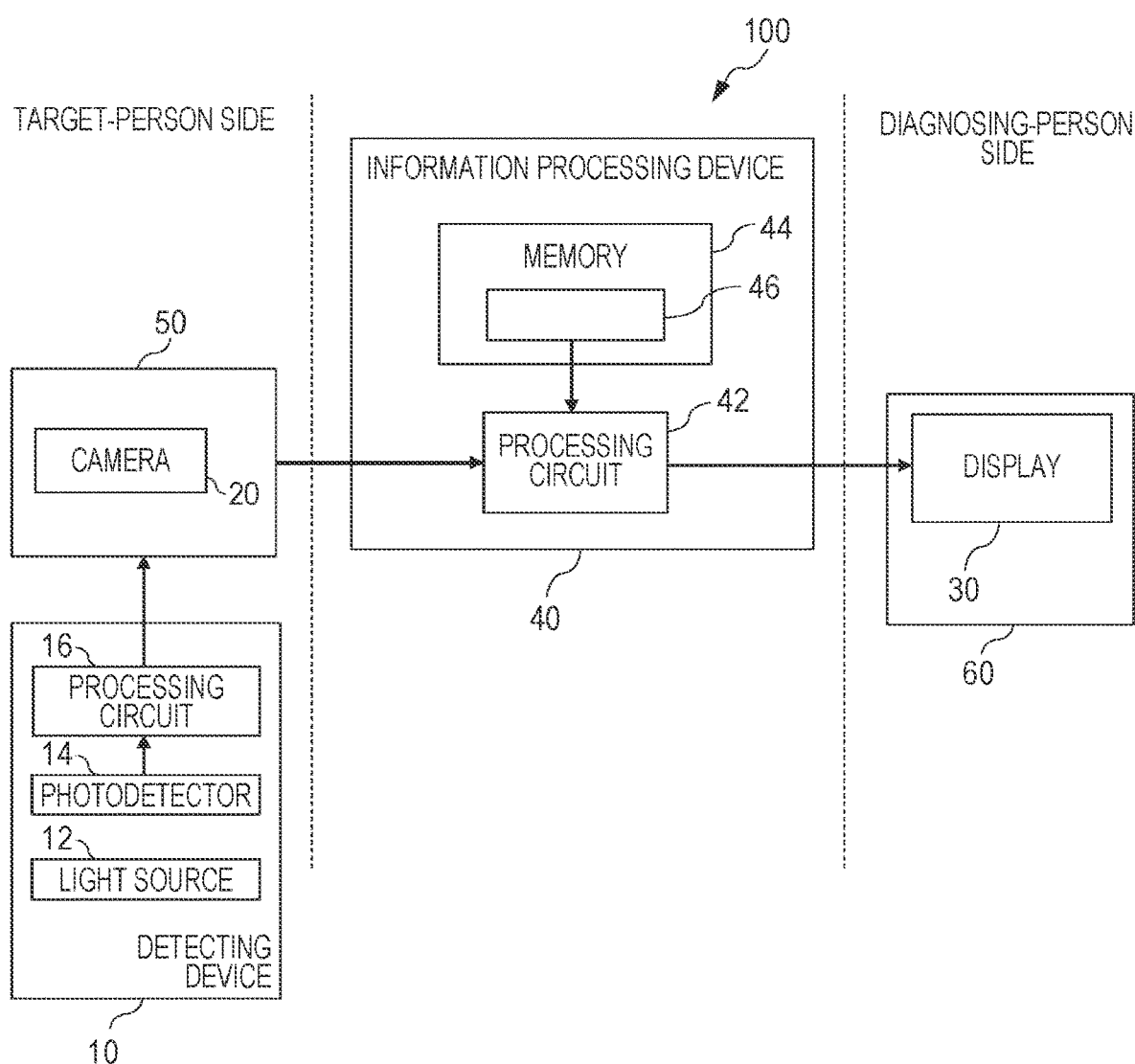
FIG. 6 is a block diagram illustrating a configuration example of an information processing system using the target-person's computer illustrated in FIG. 5.

FIG. 6 is a block diagram illustrating a configuration example of an information processing system using the target-person's computer 50 illustrated in FIG. 5. Since the detecting device 10 is connected to the target-person's computer 50, the processing circuit 16 is connected to the processing circuit 42 in the information processing device 40 via the target-person's computer 50. In such a configuration, the information processing device 40 obtains the cerebral blood flow information from the detecting device 10 via the target-person's computer 50, that is, the first computer.

Figure 7:
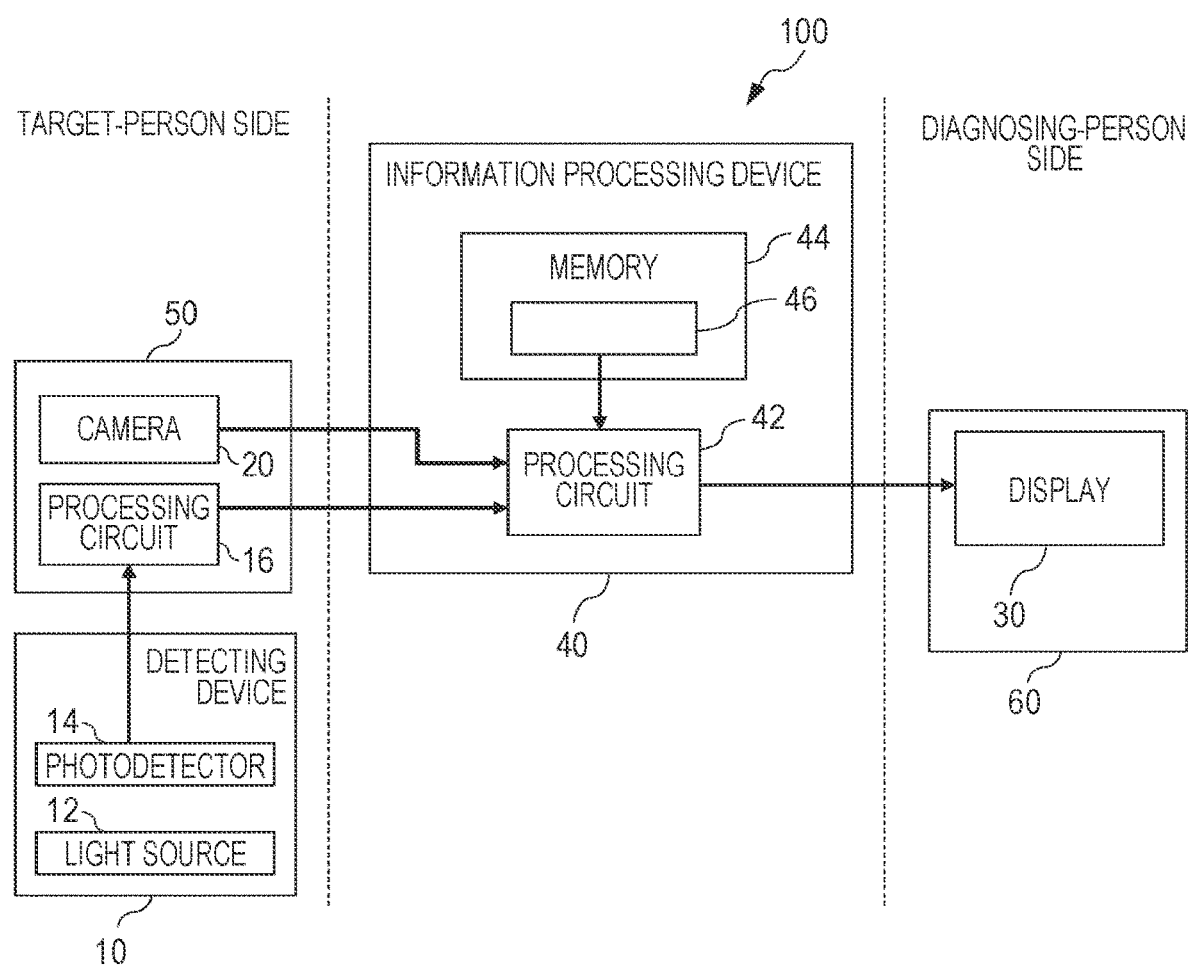
FIG. 7 is a block diagram illustrating a modification of the information processing system illustrated in FIG. 6.

FIG. 7 is a block diagram illustrating a modification of the information processing system illustrated in FIG. 6. In the example illustrated in FIG. 7, the processing circuit 16 is provided in the target-person's computer 50, not in the detecting device 10. The raw data described above is sent from the photodetector 14 to the processing circuit 16 (e.g., a CPU or a DSP) in the target-person's computer 50. The processing circuit 16 generates cerebral blood flow information, based on the raw data, and transmits the cerebral blood flow information to the processing circuit 42 in the information processing device 40. In such a configuration, the information processing device 40 obtains the cerebral blood flow information from the target-person's computer 50. However, assuming that the target-person's computer 50 is one part of the detecting device 10, it may be thought that the information processing device 40 obtains the cerebral blood flow information from the detecting device 10.

Figure 8:
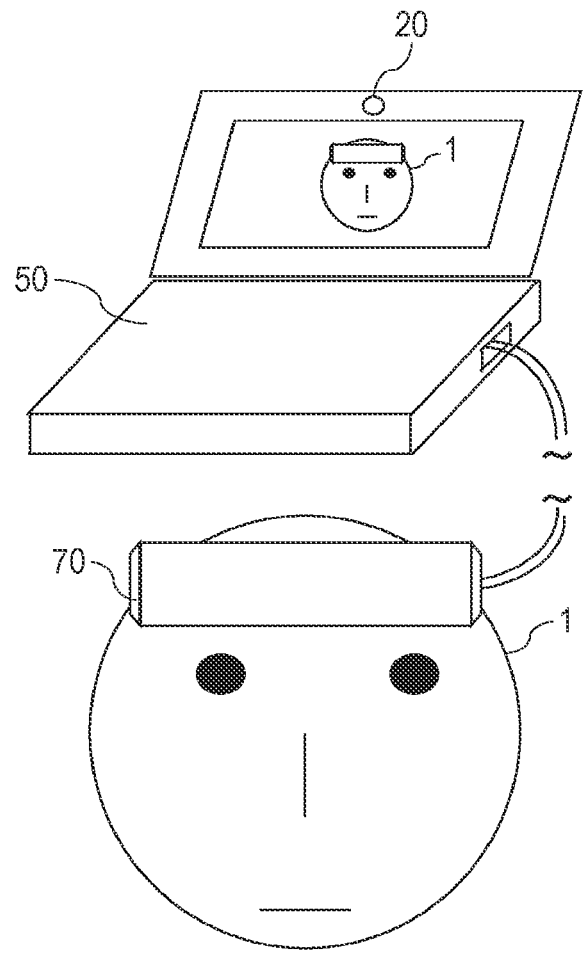
FIG. 8 is a diagram illustrating an example using a head-mounted device.

FIG. 8 is a diagram illustrating yet another modification. In the example illustrated in FIG. 8, the detecting device 10 is built into a head-mounted device 70. The camera 20 is built into the target-person's computer 50. For diagnosis, the target person 1 wears the head-mounted device 70 and starts up a predetermined application.

Figure 9:
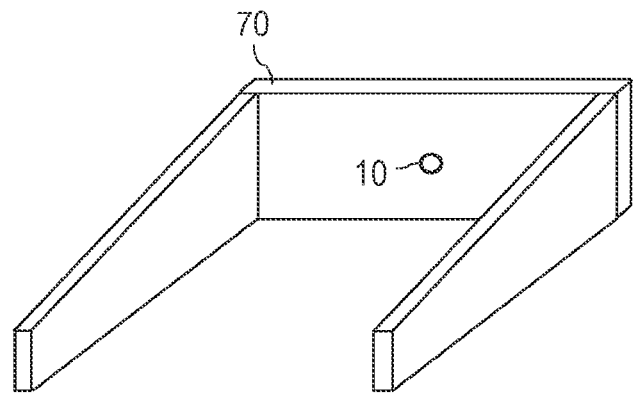
FIG. 9 is a view schematically illustrating a configuration example of the head-mounted device.

FIG. 9 is a view schematically illustrating the configuration of the head-mounted device 70. The head-mounted device 70 has the detecting device 10 at a position that opposes the forehead portion of the target person 1 when the head-mounted device 70 is worn. According to such a configuration, there are following advantages in addition to the advantages in the example illustrated in FIG. 5. First, since the forehead of the target person 1 is covered by the head-mounted device 70, influences of ambient light can be reduced even when it is used outdoors. The head-mounted device 70 may also be a head-mounted display device. In such a case, through virtual reality, natural diagnosis as if a physician is on site can be performed even from a remote location. It is also possible to perform a new task taking advantage of features of the virtual reality.

According to each configuration example described above, the information processing device 40 can simultaneously obtain a face image and a cerebral blood flow image of the target person 1 and can cause the images to be displayed on the display 30. This allows accurate diagnosis to be performed even from a remote location, as in a case in which the diagnosing person directly diagnoses the target person 1.

[Operation]

Next, a description will be given of an example of the operation of the information processing system in the present embodiment. In the following description, the configurations illustrated in FIGS. 7 and 8 are assumed to be employed by way of example. Information of the concentration of oxygenated hemoglobin and the concentration of deoxygenated hemoglobin is assumed to be generated as the cerebral blood flow information.

Figure 10:
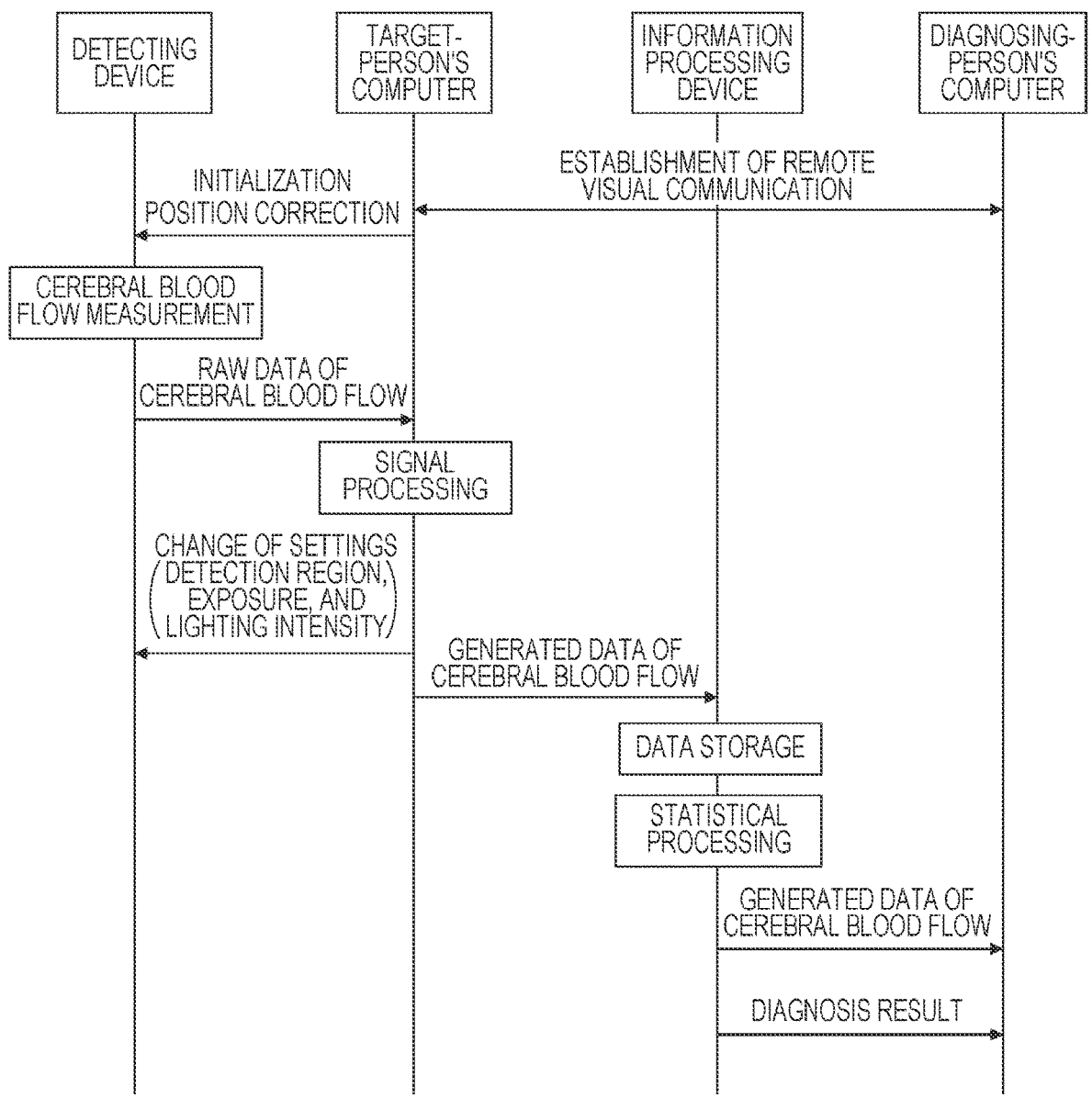
FIG. 10 is a sequence diagram illustrating an overview of operations of the devices in remote diagnosis in the exemplary embodiment of the present disclosure.

FIG. 10 is a sequence diagram illustrating an overview of the operations of the devices in remote diagnosis between the target person 1 and a diagnosing person in the present embodiment. First, remote visual communication is established between the target-person's computer 50 and the diagnosing-person's computer 60. This remote visual communication can be performed, for example, by using a video calling application, such as Skype (registered trademark). When the visual communication is established, the target-person's computer 50 transmits a control signal for initialization and position correction to the detecting device 10. The initialization means an operation for adjusting the measurement range of the detecting device 10. The position correction means adjustment for correcting the position of the target portion of the target person 1 to an appropriate position relative to the detecting device 10. The concentration of oxygenated hemoglobin and the concentration of deoxygenated hemoglobin differ from individual to individual. Also, the characteristics of the light source 12 and the photodetector 14 in the detecting device 10 may vary depending on an environmental condition, such as a temperature. Thus, before starting each measurement, the target-person's computer 50 adjusts various parameters, such as the amount of light emitted from the light source 12 or the exposure time of the photodetector 14, so that the measurement value of the cerebral blood flow falls within a certain range. In addition, in accordance with the position of the target portion which changes depending on the physical constitution or the seated position of the target person 1, the target-person's computer 50 adjusts a region on which the measurement is to be performed. When the position of the target portion of the target person 1 is not appropriate, the target-person's computer 50 may display, for example, a message to that effect on the display. When such a message is displayed, the target person 1 adjusts the position of the target portion to an appropriate position by adjusting the seated position or wearing the head-mounted device 70 again.

The detecting device 10 measures the cerebral blood flow of the target person 1 and transmits raw data of the cerebral blood flow to the target-person's computer 50. The processing circuit 16 in the target-person's computer 50 performs signal processing using raw data output from the detecting device 10, to generate data of the cerebral blood flow based on the raw data. In the signal processing, predetermined arithmetic operations based on the first and second electrical signals are performed to determine the concentration of oxygenated hemoglobin and the concentration of deoxygenated hemoglobin. After the signal processing, the target-person's computer 50 transmits a control signal for changing the settings, such as a detection region, exposure, and a lighting intensity, to the detecting device 10, when necessary. Cases in which the transmission of the control signal is necessary include, for example, a case in which the distance between the target person 1 and the detecting device 10 changes from the distance before the measurement and a case in which the amount of ambient light changes from the amount of ambient light before the measurement.

After the signal processing, the processing circuit 16 in the target-person's computer 50 transmits the generated data (i.e., the cerebral blood flow information) of the cerebral blood flow to the information processing device 40 through the network. The processing circuit 42 in the information processing device 40 stores the data in the memory 44. The information processing device 40 performs statistical processing based on the data accumulated up to that point in time, to assess the psychological state (e.g., the presence/absence of a mental disorder and the type thereof) of the target person 1. For example, data of changes over time in cerebral blood flow of a large number of target people and/or data of a spatial distribution of the cerebral blood flow are recorded to a recording medium for respective various races, genders, medical conditions in association with the medical conditions at the respective points in time. The processing circuit 42 in the information processing device 40 can assess the state of the target person 1 by comparing the current data of the cerebral blood flow of the target person 1 with the accumulated past data. A result of this assessment is referred to as a "diagnosis result". The information processing device 40 transmits the second image data, which is the generated data of the cerebral blood flow, and data indicating the diagnosis result to the diagnosing-person's computer 60. The diagnosing-person's computer 60 causes the display 30 to display the cerebral blood flow information and an image indicating the diagnosis result.

Next, a description will be given of a flow of remote diagnosis performed between a target person and a diagnosing person.

Figure 11:
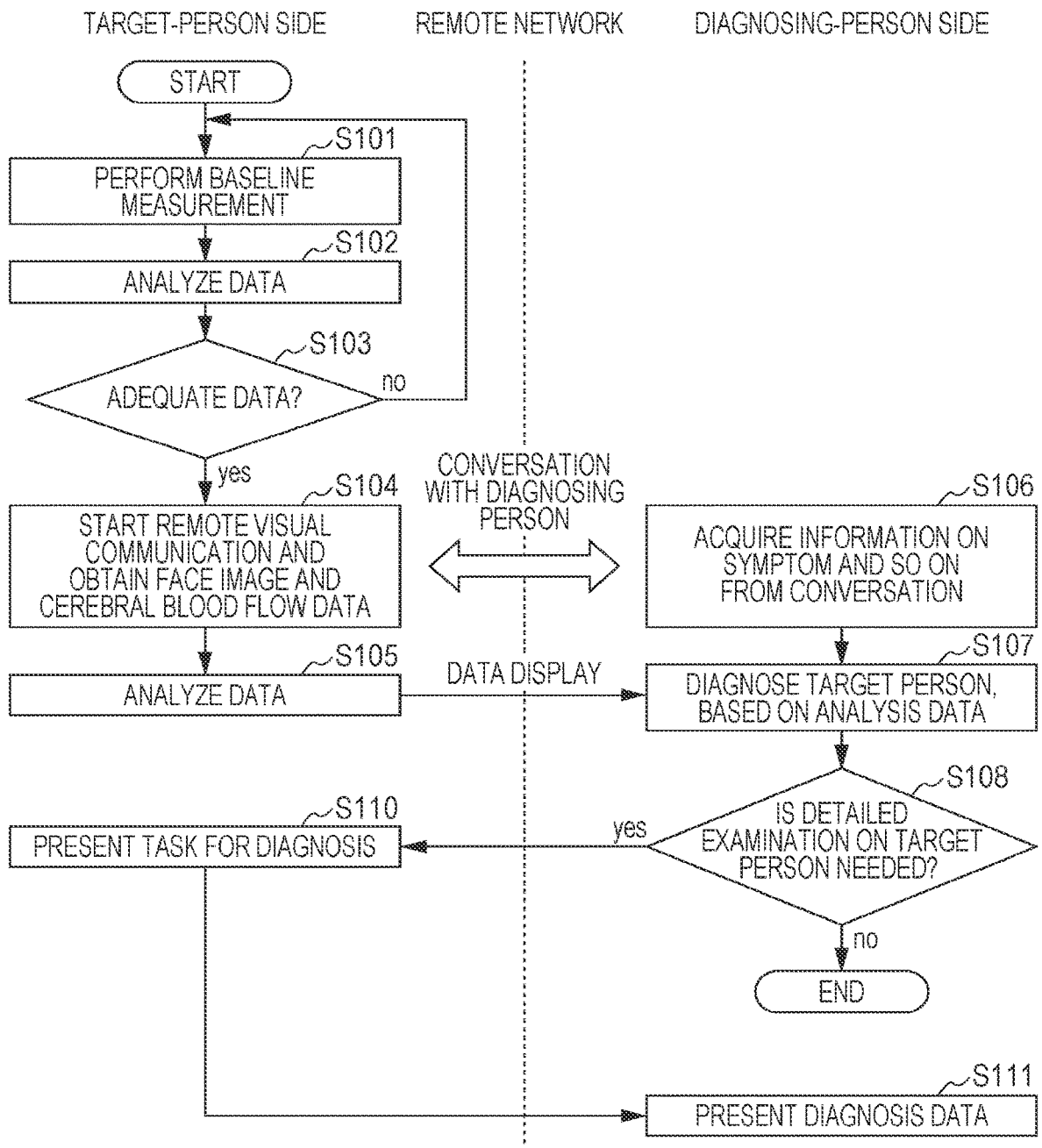
FIG. 11 is a flowchart illustrating one example of a flow of remote diagnosis in the exemplary embodiment of the present disclosure.

FIG. 11 is a flowchart illustrating one example of a flow of remote diagnosis between a target person and a diagnosing person in the present embodiment.

First, the target-person's computer 50 and the detecting device 10 perform baseline measurement (step S101). The baseline measurement refers to measurement for obtaining an initial value of the cerebral blood flow information. The target person 1 performs a simple task, such as calculation, for a certain period of time (e.g., two minutes). During the period of time, the detecting device 10 illuminates the forehead portion of the target person 1 with light and detects reflection light therefrom. Based on a signal output from the photodetector 14 in the detecting device 10, the processing circuit 16 determines the concentration of oxygenated hemoglobin and the concentration of deoxygenated hemoglobin.

Next, the processing circuit 16 analyzes data of the determined cerebral blood flow and checks motion of the target person 1 or the presence/absence of noise (step S102). For example, the motion of the target person 1 can be known in a manner described below. In nature, the concentration of oxygenated hemoglobin and the concentration of deoxygenated hemoglobin exhibit opposite changes over time. Accordingly, when changes over time in both the concentration of oxygenated hemoglobin and the concentration of deoxygenated hemoglobin increase or decrease, it can be determined that the target person 1 is moving.

Based on the analysis result, the processing circuit 16 determines whether or not the data is adequate (step S103). If the data is not adequate, steps S101 to S103 are performed again.

If the data is adequate, remote communication is started between the target person 1 and the diagnosing person. The camera 20 obtains data of a face image of the target person 1, and the detecting device 10 obtains the data of the cerebral blood flow of the target person 1 (step S104). These pieces of data are transmitted to the processing circuit 42 in the information processing device 40. The processing circuit 42 transmits image data based on the pieces of data to the display 30 of the diagnosing-person's computer 60. As a result, the face image of the target person 1 and an image indicating information of the cerebral blood flow are displayed on the display 30 of the diagnosing-person's computer 60. Thus, the diagnosing person performs medical examination on the target person 1 through video calling therewith and acquires information on a symptom and so on through conversation with the target person 1 (step S106).

The processing circuit 16 in the target-person's computer 50 further analyzes the cerebral blood flow data obtained in step S104 and causes the analysis result to be displayed on the display 30 of the diagnosing-person's computer 60 (step S105). Based on the displayed analysis data, the diagnosing person diagnoses the target person 1 (step S107). Based on the analysis data, the diagnosing person determines whether or not more detailed examination on the target person 1 is needed (step S108). If detailed examination on the target person 1 is not needed, the diagnosis ends.

If it is determined that detailed examination on the diagnosing person is needed, the information processing device 40 presents task information, such as a task for diagnosis, to an output device of the target-person's computer 50 (step S110). The output device of the target-person's computer 50 is, for example, a display or a microphone. The task for diagnosis checks changes in a blood flow rate between a state in which the target person 1 is relaxing and a state in which the target person 1 is working on a test.

It is known that the functions of the brain are localized to some degree. Thus, the task for diagnosis is designed depending on what state of the target person 1 is to be known. For example, an N-back task may be used as the task for diagnosis. The N-back task is also called a continuous performance test and is a test in which a target person responds to a stimulus presented N-stimuli earlier. In the N-back test, it is difficult to memorize the test, and a cerebral-blood-flow change reduction due to habituation is less likely to occur. The difficulty increases, as N increases. Thus, the difficulty of the test can be set easily.

After the target person 1 performs the task for diagnosis, the target-person's computer 50 presents diagnosis data and a diagnosis result to the display 30 of the diagnosing-person's computer 60 via the information processing device 40 (step S111). The diagnosis result is obtained by verifying the diagnosis data against a database. This makes it possible to assess the type and the probability of the target person 1 having a disease.

Next, a description will be given of events that are disturbance factors that affect the measurement result of cerebral blood flow of the target person 1 during the diagnosis task.

The events are broadly classified into events caused by the measurement environment of the target person 1 side and events caused the target person 1 himself or herself.

Examples of the events caused by the measurement environment of the target person 1 side include a large ambient sound and a room lighting change due to turning on or off of a light. For diagnosing depression, changes over time in the cerebral blood flow during a diagnosis task are used. When changes over time in the cerebral blood flow vary owing to a measurement environment, there is a possibility that the change affects the diagnosis.

Examples of the events caused by the target person 1 himself or herself include large motion of the body of the target person 1 and a decline in the concentration power of the target person 1 during a diagnosis task. Relative positional displacement between the target person 1 and the photodetector 14 or a decline in the concentration power of the target person 1 can affect the cerebral blood flow measurement.

Each of the events described above can be detected based on at least one of a plurality of pieces of data below. The plurality of pieces of data includes image data from the camera 20 in the target-person's computer 50, image data from another camera connected to or built into the target-person's computer 50, and audio data from a microphone connected to or built into the target-person's computer 50. For example, the above-described events can be detected by a camera for videophone used in remote diagnosis, another camera, or a microphone.

Next, a description will be given of an example of an event determination method.

The events caused by a large ambient sound can be determined in the following manner. When the volume of sound detected by a microphone exceeds a given threshold with reference to the volume of voice in conversation between the target person 1 and the diagnosing person, it is determined that an event has occurred.

The events caused by a room lighting change can be determined in the following manner. When illuminance changes from illuminance in a camera image by a certain amount or more, it is determined that an event has occurred.

The events caused by large motion of the body of the target person 1 can be determined in the following manner. When the relative position between the target person 1 and the photodetector 14 changes in a camera image by a certain amount or more, it is determined that an event has occurred. The certain amount is, for example, ±3 cm.

The events caused by a decline in the concentration power of the target person 1 can be determined in the following manner. When the line-of-sight of the target person 1 changes by a certain amount, it is determined that an event has occurred.

The above-described events may be determined by artificial intelligence (AI) built into the information processing device 40 or the target-person's computer 50.

[Display Example]

Next, a description will be given of an example displayed on the display 30 of the diagnosing-person's computer 60.

Figure 12A:
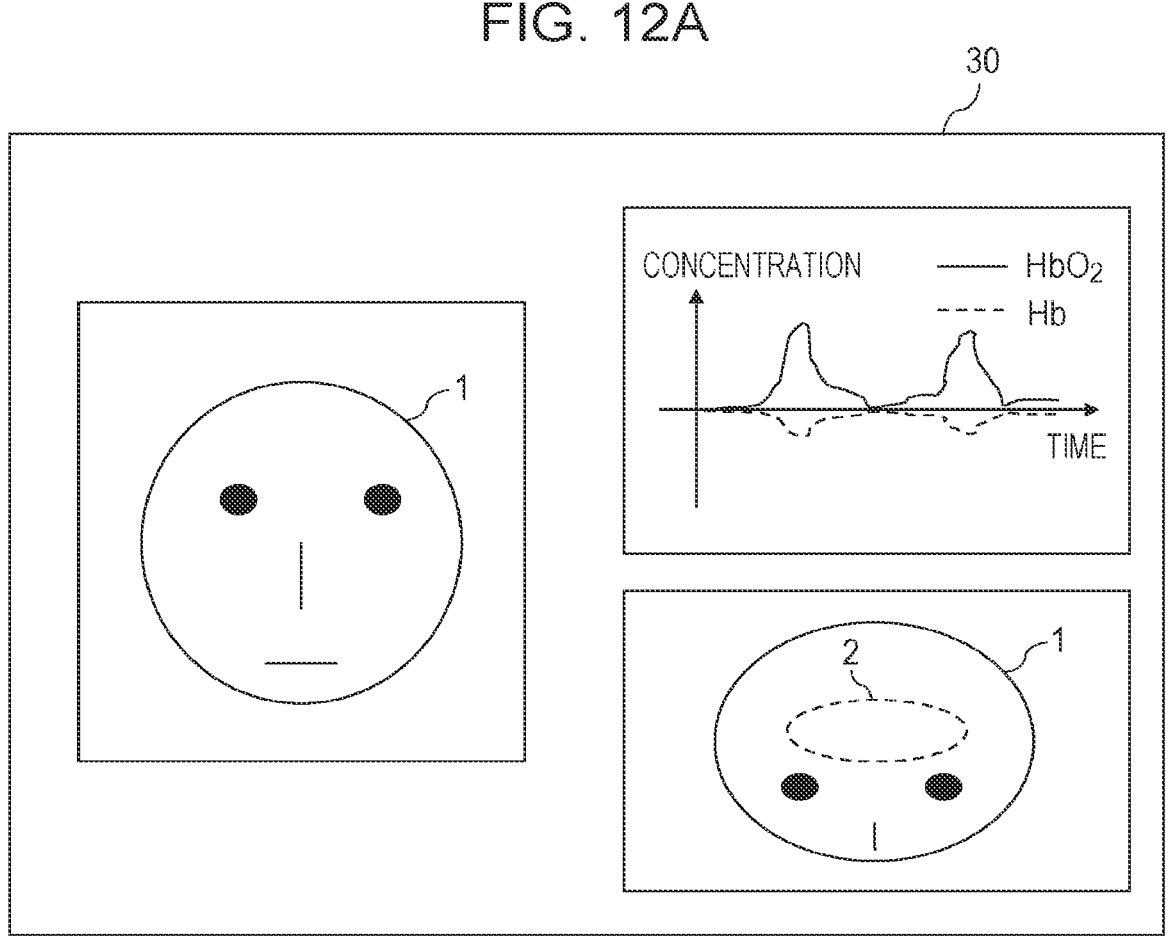
FIG. 12A is a view schematically illustrating an example displayed on the display of the diagnosing-person's computer.

FIG. 12A is a view schematically illustrating an example displayed on the display 30 of the diagnosing-person's computer 60. In the example illustrated in FIG. 12A, a moving image of the face of the target person 1 is displayed at the left side on the screen of the display 30, a graph indicating changes over time in the cerebral blood flow is displayed on the upper right, and the target portion 2 of the target person 1 is displayed at the lower right. In the upper-right graph illustrated in FIG. 12A, the solid line represents changes over time in the concentration of oxygenated hemoglobin, and the dashed line represents changes over time in the concentration of deoxygenated hemoglobin. What is shown in the graph is not limited to the example illustrated in FIG. 12A, and the graph may show changes over time in the concentration of one of the oxygenated hemoglobin and the deoxygenated hemoglobin. The upper-right image illustrated in FIG. 12A may indicate changes over time in cerebral blood flow obtained from one portion of the target portion 2 and may indicate changes over time in an average cerebral blood flow obtained from a plurality of portions or regions of the target portion 2. The waveform of changes over time in the cerebral blood flow may be denoted by a cursor indicating a current point in time or a representation indicating the period of a task.

Figure 12B:
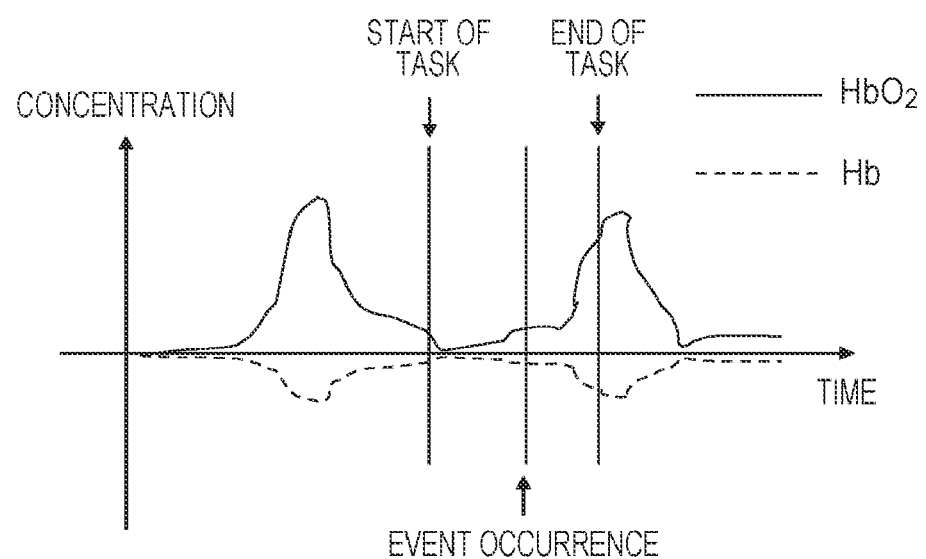
FIG. 12B is a graph schematically illustrating a modification of the upper-right image illustrated in FIG. 12A.

FIG. 12B is a graph schematically illustrating a modification of the upper-right image illustrated in FIG. 12A. In the example illustrated in FIG. 12B, the start and the end of a task and occurrence of an event are denoted by vertical lines.

As illustrated in FIG. 12B, the upper-right image illustrated in FIG. 12A may include a correspondence relationship between changes over time in the cerebral blood flow and a period in which task information is output. This clarifies changes over time in the cerebral blood flow of the target person 1 during the task. The period in which the task is output corresponds to a period from the start of the task for diagnosis to the end of the task for diagnosis.

As illustrated in FIG. 12B, the upper-right image illustrated in FIG. 12A may include a correspondence relationship between changes over time in the cerebral blood flow and a period in which an event occurs. This clarifies influences that the event has on changes over time in the cerebral blood flow of the target person 1. When the period in which the event occurs is short, only one portion may be shown.

Figure 13:
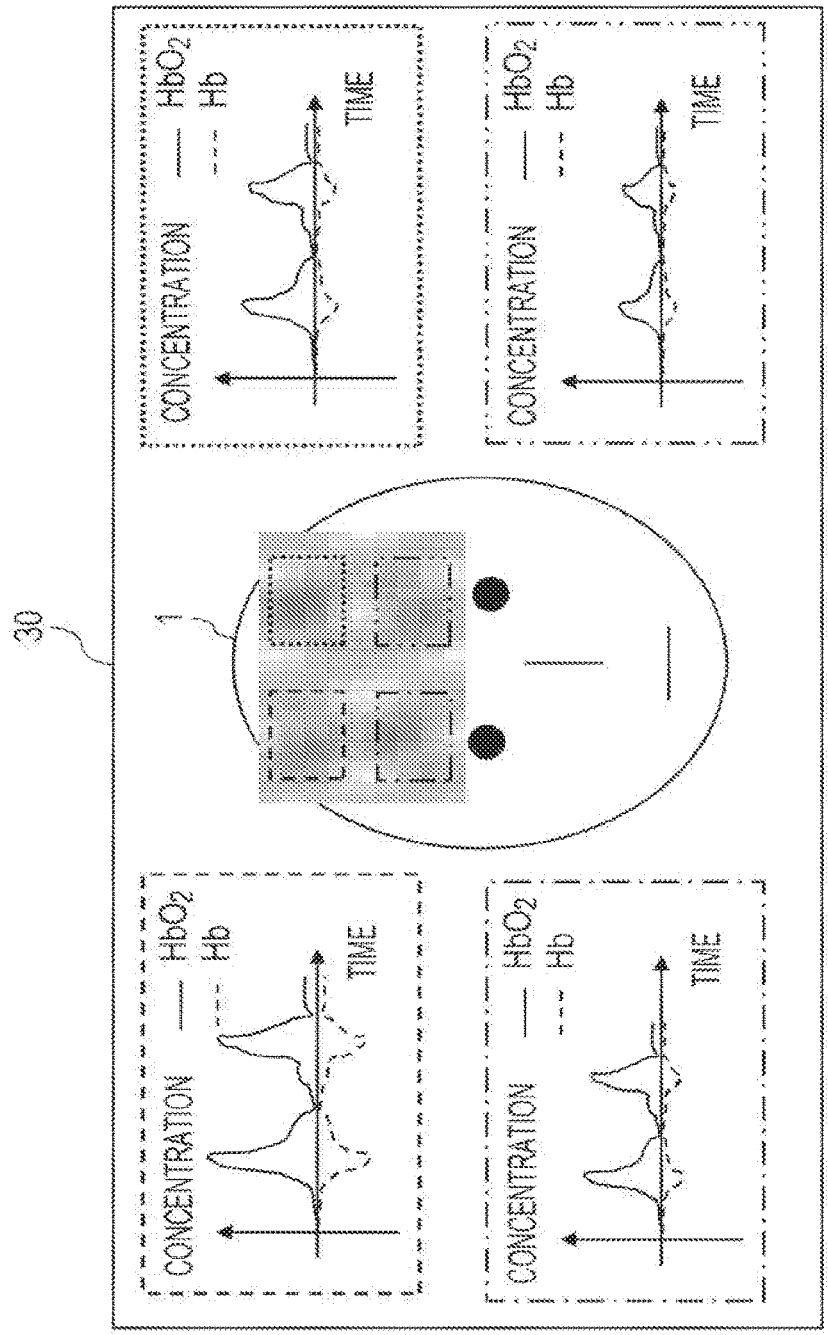
FIG. 13 is a view schematically illustrating another example displayed on the display of the diagnosing-person's computer.

FIG. 13 is a view schematically illustrating another example displayed on the display 30 of the diagnosing-person's computer 60. In the example illustrated in FIG. 13, an image indicating two-dimensional concentration distributions of cerebral blood flow of the target portion 2 is combined with a moving image of the face of the target person 1, and the resulting image is displayed. Each two-dimensional concentration distribution may be, for example, an oxygenated-hemoglobin concentration distribution. In addition, a plurality of graphs indicating changes over time in the cerebral blood flow in a plurality of regions in the target portion 2 is displayed around the moving image of the face of the target person 1. These graphs each show changes over time in an average concentration of oxygenated hemoglobin and an average concentration of deoxygenated hemoglobin in each region.

In the example illustrated in FIG. 13, the plurality of graphs indicating changes over time in the cerebral blood flow and the plurality of regions in the target portion 2 are associated with each other by different types of surrounding lines (a dashed line, a dotted line, a dashed-dotted line, and a chain double-dashed line). This makes it possible to determine which graph indicates in which region changes over time in the cerebral blood flow occurred. The association is not limited to the surrounding lines and may be performed using, for example, colors, numbers, or characters.

In the present embodiment, images indicating cerebral blood flow information expressed as graphs are displayed in real time, as illustrated in FIGS. 12A, 12B, and 13. Thus, before measurement, a specific region, which is a cerebral region for expressing the cerebral blood flow information as a graph, is selected. The specific region is, for example, a cerebral region in which a cerebral blood flow rate changes significantly depending on a task. The cerebral region differs from individual to individual.

The following description will be given of an example of a method for determining the specific region.

When a cerebral region that becomes active significantly according to a disease or a symptom is known from statistical data, a specific region pre-expressed as a graph before diagnosis can be selected from candidates. For example, the name of a portion of at least one specific region corresponding to a disease or a symptom is set for a candidate. Herein, the set candidates are referred to as "set items". The processing circuit 42 causes the display 30 of the diagnosing-person's computer 60 to display the set items. Instead of displaying the set items, at least one specific region surrounded by a line may be displayed, as illustrated in FIG. 13. Furthermore, the set items may be the names of diseases or symptoms.

The diagnosing person inputs input information regarding the set items to an input device connected to or built into the diagnosing-person's computer 60. The input device is, for example, a user interface, such as a keyboard or a mouse. The processing circuit 42 obtains the input information and determines a specific region in accordance with the input information. Only the determined specific region is displayed on the display 30 of the diagnosing-person's computer 60, with the specific region being surrounded by a line. A plurality of cerebral regions that become active according to a disease or a symptom may exist. Accordingly, the number of specific regions that are determined does not necessarily have to be one and may be two or more.

Another possible example of the method for determining the specific region may be a method for checking the specific region by making the target person 1 perform a preliminary task, such as simple calculation, before the task for diagnosis. For example, in step S104 illustrated in FIG. 11, the processing circuit 42 causes the display of the target-person's computer 50 to output preliminary task information indicating a preliminary task. The target person 1 performs the preliminary task. The processing circuit 42 determines a specific region according to the magnitude of a change in the cerebral blood flow information of the target person 1, the change being caused by the preliminary task. For example, a region in which the cerebral blood flow information changes greater than a specified threshold may be set for the specific region. The number of specific regions that are determined does not necessarily have to be one and may be two or more. This specific-region determination method is effective when a cerebral region that becomes active according to a disease or a symptom is not known.

As described above, in the present embodiment, it is not necessary to measure cerebral blood flow in a large range in the brain of the target person 1. Herein, cerebral blood flow information related to at least one specific region in the brain of the target person 1 is referred to as "part of cerebral blood flow information".

In the present embodiment, the part of cerebral blood flow information may be selected, for example, using the above-described determination method, and the selected part of cerebral blood flow information may be expressed as a graph. Expressing the part of cerebral blood flow information as a graph can enhance the efficiency of the diagnosis.

In the present embodiment, the part of cerebral blood flow information may be selected, for example, using the above-described determination method, and the selected part of cerebral blood flow information may be transmitted from the target-person's computer 50 to the diagnosing-person's computer 60 through a remote network. Transmitting the part of cerebral blood flow information before it is expressed as a graph can reduce the amount of communication. As a result, it is possible to reduce delay in communication.

The target person 1, instead of the diagnosing person, may select the part of cerebral blood flow information. In such a case, the set items may be displayed on the display of the target-person's computer 50.

When the display illustrated in FIG. 13 is to be performed, the photodetector 14 is implemented by an image sensor having sensitivity to light (e.g., near-infrared light) emitted from the light source 12. The image sensor includes light-receiving elements that are arranged two-dimensionally. The light-receiving elements are, for example, photoelectric converting elements, such as photodiodes, and output electrical signals corresponding to the amounts of light that is received. A collection of the electrical signals output from the light-receiving elements is treated as image signals. In order to obtain cerebral blood flow information of a plurality of regions in the target portion 2, the light source 12 illuminates the plurality of regions with light. The processing circuit 16 generates pieces of cerebral blood flow information for the respective regions, based on the signals output from the image sensor, and outputs the pieces of cerebral blood flow information.

When a face image of the target person 1 and an image indicating changes in the cerebral blood flow of the target person 1 are displayed at the same time, as illustrated in FIGS. 12A, 12B, and 13, the diagnosing person can more effectively diagnose the psychological state of the target person 1.

Figure 14:
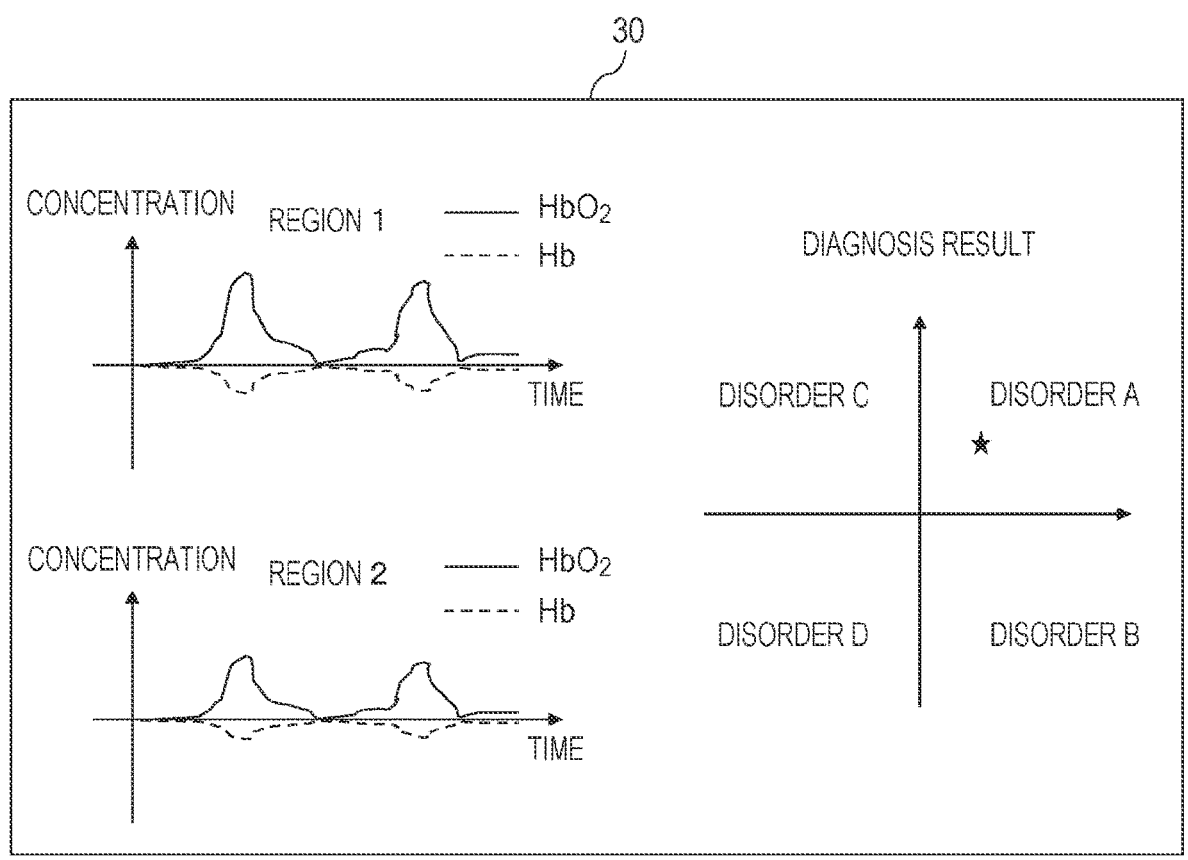
FIG. 14 is a view schematically illustrating another example displayed on the display of the diagnosing-person's computer.

FIG. 14 is a view schematically illustrating yet another example displayed on the display 30 of the diagnosing-person's computer 60. More specifically, the example in FIG. 14 illustrates a graph showing changes over time in average concentrations of oxygenated hemoglobin and deoxygenated hemoglobin in a region 1 of the target portion 2, a graph showing changes over time in average concentrations of oxygenated hemoglobin and deoxygenated hemoglobin in a region 2 of the target portion 2, and a chart showing a diagnosis result of a target person. In the example illustrated in FIG. 14, the region 1 is a frontal region of the head, and the region 2 is a temporal region. The star sign in the right-side chart illustrated in FIG. 14 indicates a disorder that is assessed to affect the target person. With which disorder the target person is affected is assessed from changes over time in the concentration of oxygenated hemoglobin and the concentration of deoxygenated hemoglobin in each region. The information processing device 40 may assess the psychological state of the target person or the probability of the target person having a disease and may cause the display 30 to display the assessment result.

In response to an operation of the diagnosing person, the diagnosing-person's computer 60 may switch the image displayed on the display 30. For example, only a face image may be initially displayed and be switched to a cerebral blood flow image or the image illustrated in FIG. 14 in accordance with an operation of the diagnosing person, or an image obtained by combining a face image and a cerebral blood flow image together may be displayed. In such a case, when the diagnosing person performs an operation for switching the image while a face image of the target person 1 is displayed on the display 30, the diagnosing-person's computer 60 transmits, to the information processing device 40, a signal indicating that the displayed image to be switched. Upon receiving the signal, the information processing device 40 causes the display 30 to display an image indicating the state of the cerebral blood flow, in addition to the face image or instead of the face image.

What is claimed is:

1. An information processing method comprising:
obtaining a first moving image indicating at least one portion of a face of a person from a camera;
generating a second moving image indicating changes over time in a cerebral blood flow of the person based on information from a detector that detects light from the person; and displaying an output image including the first moving image and the second moving image on a display,
wherein a frame rate of the second moving image is lower than a frame rate of the first moving image.

2. The information processing method according to claim 1, wherein the camera and the detector are connected to or built into a first computer, and the display is connected to or built into a second computer connected to the first computer through a network.

3. The information processing method according to claim 2, wherein the second computer switches an image displayed on the display in response to an operation on the second computer, and
the information processing method further comprises
causing the first moving image to be displayed on the display; and
causing the second moving image to be displayed on the display in addition to the first moving image or instead of the first moving image, in response to the operation.

4. The information processing method according to claim 1, further comprising:
obtaining input information regarding a disease name or a symptom name; and
determining, based on the input information, a region in a brain of the person,
wherein the cerebral blood flow corresponds to the region.

5. The information processing method according to claim 1, wherein the output image is obtained by combining the first moving image and the second moving image.

6. The information processing method according to claim 1, further comprising:
assessing at least one selected from the group consisting of a psychological state of the person and a probability of the person having a disease, based on the cerebral blood flow; and displaying a result of the assessment on the display.

7. The information processing method according to claim 1, wherein
the second moving image indicates changes over time in numerically expressed the cerebral blood flow.

8. The information processing method according to claim 1, wherein
the second moving image includes one or more graphs whose vertical axis corresponds to concentration of hemoglobin of the cerebral blood flow and whose horizontal axis corresponds to time.

9. An information processing system comprising:
a camera;
a detector that detects a light from a person; and
a circuit;
wherein the circuit
obtains a first moving image indicating at least one portion of a face of a person from a camera;
generates a second moving image indicating changes over time in a cerebral blood flow of the person based on information from a detector that detects light from the person; and
causes a display to display an output image including the first moving image and the second moving image,
wherein a frame rate of the second moving image is lower than a frame rate of the first moving image.

* * * * *